United States Patent
Josephson et al.

(10) Patent No.: US 6,640,364 B1
(45) Date of Patent: Nov. 4, 2003

(54) PEDESTAL FOR USE WITH PATIENT TRANSPORT SYSTEM FOR MULTIPLE IMAGING SYSTEMS

(75) Inventors: Sean S. Josephson, Brookfield, WI (US); Jason I. Subirana, New Berlin, WI (US)

(73) Assignee: GE Medical Systems Global Technololgy Company, LLC, Waukesha, WI (US)

( * ) Notice: Subject to any disclaimer, the term of this patent is extended or adjusted under 35 U.S.C. 154(b) by 49 days.

(21) Appl. No.: 09/999,204

(22) Filed: Nov. 30, 2001

(51) Int. Cl.[7] .................................................. A61B 6/04
(52) U.S. Cl. ......................... 5/601; 5/81.1 HS; 5/86.1; 378/209
(58) Field of Search .............................. 5/601, 81.1 HS, 5/86.1, 81.1 R, 83.1, 600; 378/209

(56) References Cited

U.S. PATENT DOCUMENTS

| | | | |
|---|---|---|---|
| 3,167,789 A | * 2/1965 | Wicks | 5/81.1 HS |
| 4,105,923 A | * 8/1978 | Hynes, Jr. | 378/20 |
| 4,222,132 A | * 9/1980 | Crim et al. | 5/81.1 R |
| 4,641,823 A | * 2/1987 | Bergman | 5/81.1 HS |
| 4,671,728 A | * 6/1987 | Clark et al. | 414/401 |
| 4,805,626 A | * 2/1989 | DiMassimo et al. | 600/415 |
| 4,944,501 A | * 7/1990 | Sireul et al. | 5/601 |
| 5,475,884 A | * 12/1995 | Kirmse et al. | 5/601 |
| 5,842,987 A | * 12/1998 | Sahadevan | 600/407 |

\* cited by examiner

Primary Examiner—Michael F. Trettel
(74) Attorney, Agent, or Firm—Foley & Lardner; Peter J. Vogel; Micael A. Della Penna

(57) ABSTRACT

A pedestal for use with a patient transport system for multiple imaging systems can include a support member configured to support a patient or object of interest, an elongated planar member coupled to the support member and configured to removably couple and slidably engage an elongated cradle member, and a docking assembly coupled to the elongated planar member configured to engage the receipt of and the removal of the elongated cradle member supportable by the elongated planar member.

13 Claims, 4 Drawing Sheets

PEDESTAL FOR USE WITH PATIENT TRANSPORT SYSTEM FOR MULTIPLE IMAGING SYSTEMS

BACKGROUND OF THE INVENTION

The present invention relates generally to imaging systems and imaging techniques. More specifically, the present invention relates to a pedestal for use in a patient transport system for multiple imaging systems.

Currently, patients and objects can be imaged using a wide variety of different imaging technologies. Such imaging technologies can include magnetic resonance imaging (MRI), computer tomography (CT), x-ray imaging, and others. Each imaging technology has unique advantages and disadvantages in imaging certain types of physiological or physical characteristics.

As an example, x-ray images of human patients have excellent spatial and temporal resolution and, therefore, show features such as coronary arteries with extreme clarity. MRI images provide excellent soft tissue contrast with no exposure to ionizing radiation. MRI images also provide three-dimensional image acquisition. One advantage of x-ray images is that they can show vessels which are too small to be seen on MRI images.

In some imaging applications, multiple imaging modalities are desirable. During interventional procedures, x-ray imaging is preferred because of the easy access doctors have to the patient for guide wire and catheter manipulation. However, to obtain the improved soft tissue contrast and three-dimensional imaging of MRI, MRI images are required. In particular, x-ray imaging can be used to guide invasive devices and MRI can monitor the results of the therapy in the surrounding tissues.

When combining x-ray imaging and MRI technologies in the interventional environment, there is as need for quickly moving the patient between the x-ray system and the MR system without excessive anatomical movement and disruption of the patient. Current methods involve transferring the patient from the imaging table to a gurney for transport between the modalities. This can cause discomfort or even harm to the patient. Further, the interventional procedure can be compromised.

Accordingly, there is a need for an improved patient transport system and method for transferring a patient from a first medical imaging system to a second medical imaging system. Further, there is a need for a patient transport system and method in which the patient need not be significantly lifted or otherwise manipulated. Further still, there is a need for a patient transport system and method which minimizes x-ray absorption and optimizes image quality in an x-ray imaging system. Further yet, there is a need for a patient transport system and method which does not require transferring the patient from one tabletop to another.

There is further a need for an improved patient transport system and method which allows quick transfer of a patient in a straight-line motion between imaging modalities. Further, there is a need for a simpler, safer, and more accurate patient transfer system and method. Further still, there is a need for a patient transfer system and method in which all monitoring and support equipment is transferred with the patient, thereby eliminating any relative motion between the patient and the equipment.

The teachings hereinbelow extend to those embodiments which fall within the scope of the appended claims, regardless of whether they accomplish one or more of the above-mentioned needs.

SUMMARY OF THE INVENTION

According to another exemplary embodiment, a pedestal for supporting a patient or object of interest in an imaging system can include a support member configured to support a patient or object of interest, an elongated planar member coupled to the support member and configured to removably couple and slidably engage an elongated cradle member, and a docking assembly coupled to the elongated planar member configured to engage the receipt of and the removal of the elongated cradle member supportable by the elongated planar member.

According to another exemplary embodiment, an x-ray pedestal can include means for receiving a removable elongated patient support member, means for securing the removable elongated patient support member to a cantilevered structure, and means for transferring the removable elongated patient support member to a docked transport table.

According to another exemplary embodiment, a patient support structure for use in an imaging system can include an elongated support surface having an end compatible with a coupling arrangement on a movable transport table configured to transport a patient support structure and a coupling device configured to removably couple the patient support structure to the elongated support surface. The coupling device includes an actuator configured to disconnect the patient support structure from the elongated support surface.

Other principle features and advantages of the invention will become apparent to those skilled in the art upon review of the following drawings, the detailed description, and the appended claims.

BRIEF DESCRIPTION OF THE DRAWINGS

The exemplary embodiments will hereafter be described with reference to the accompanying drawings, wherein like numerals denote like elements, and.

DETAILED DESCRIPTION OF THE EXEMPLARY EMBODIMENTS

FIGS. 1–8 are intended to facilitate the description of exemplary patient transport systems for multiple imaging systems. In the following description, for purposes of explanation, numerous specific details are set forth in order to provide a thorough understanding of the present invention. It will be evident, however, to one skilled in the art that the exemplary embodiments may be practiced without these specific details. In other instances, well-known structures and devices are shown in diagram form in order to facilitate description of the exemplary embodiments.

Figure 1:
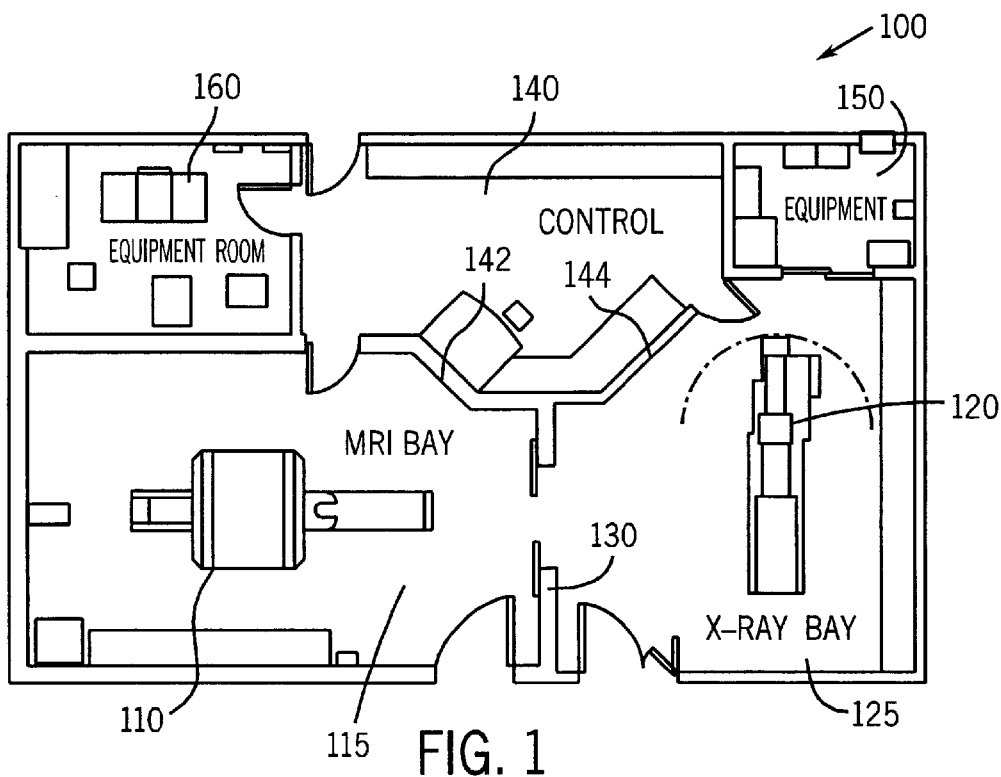
FIG. 1 is a diagrammatic representation of an X-MR suite for x-ray/MR interventional therapy and imaging in accordance with an exemplary embodiment.

FIG. 1 illustrates an X-MR suite 100 configured for x-ray/MR interventional therapy and imaging in accordance with an exemplary embodiment. X-MR suite 100 can include a magnetic resonance (MR) system 110 and a vascular x-ray system 120 in two separate bays, a MR bay 115 and a x-ray bay 125, separated by a movable door 130. MR system 110 is an assembly including an MR magnet, cryogens, RF coils, gradient coils, and other components. X-ray system 120 is an assembly including an x-ray generating device and other components.

Movable door 130 can contain shielding for radio frequency (RF) and x-rays. The RF shielding of movable door 130 is also included throughout MR bay 115 to prevent electromagnetic interference (EMI) from radiating into or out of the room. X-ray bay 125 can include lead shielding for shielding from x-rays. Accordingly, MR system 110 and x-ray system 120 can be used independently when movable door 130 is closed. Movable door 130 can be opened to allow transfer of a patient or object of interest from MR bay 115 to x-ray bay 125 or vice versa.

X-MR suite 100 can also include a control room 140 with a window 142 providing a view of MR bay 115 from control room 140 and a window 144 providing a view of x-ray bay 125 from control room 140. X-MR suite 100 can further include an equipment room 150 and an equipment room 160. In alternative embodiments, X-MR suite 100 can include other rooms, bays, or sections associated with X-MR procedures, such as, a patient holding area or storage area.

Figure 2:
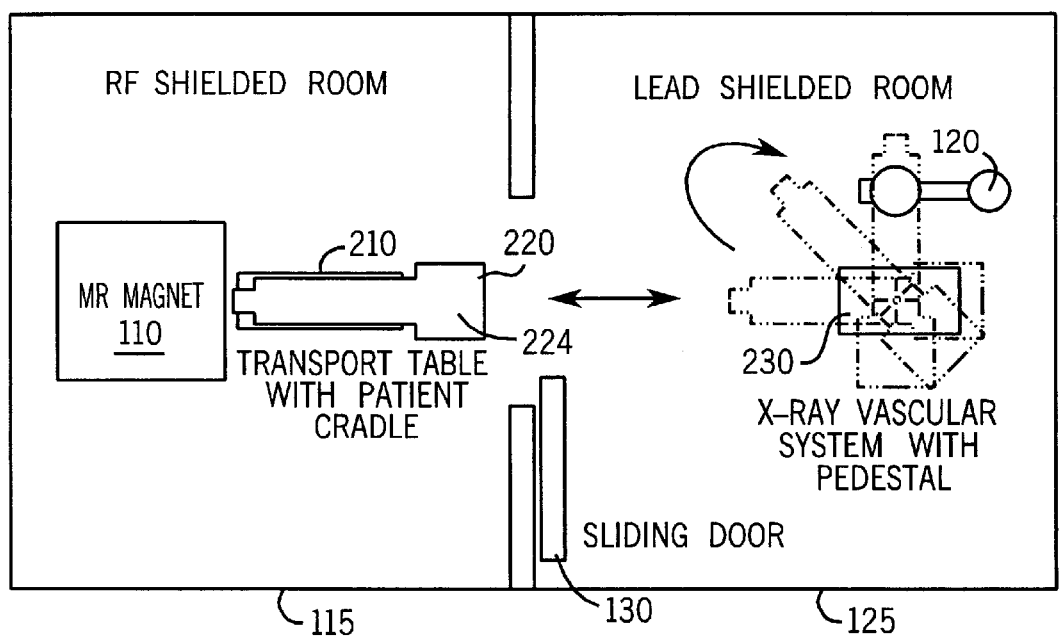
FIG. 2 is a schematic representation of a portion of the X-MR suite of FIG. 1 in accordance with an exemplary embodiment.

Referring now to FIG. 2, X-MR suite 100 further can include a patient transport table 210, a patient cradle 220, and an x-ray pedestal 230. Patient transport table 210 is preferably a wheeled cart that supports patient cradle 220 during transport between MR system 110 and x-ray system 120. Patient transport table 210 is mobile and configured to be compatible with an MR environment. For example, patient transport table 210 can be made of primarily aluminum and fiberglass.

Patient cradle 220 is latched to patient transport table 210 when moving the patient or object of interest. One end of patient transport table 210 docks with MR system 110 and the other end of patient transport table 210 docks with x-ray pedestal 230. Patient cradle 220 can be configured to be compatible with both MR and x-ray imaging systems and is capable of supporting a cantilevered patient load in the x-ray setting. Patient cradle 220 can be made of a KEVLAR™ material or some other type of aramid fiber material or shielding material.

Patient cradle 220 provides a elongated bed on which a patient or object can rest. Patient cradle 220 includes a workspace 224 at one end for ancillary equipment. X-ray pedestal 230 is part of x-ray system 120. X-ray pedestal 230 is preferably a permanently-mounted table on a fixed base with multiple axis of motion. Patient cradle 220 can move onto x-ray pedestal 230 when using x-ray system 120 to image the patient or object.

Advantageously, patient transport table 210, patient cradle 220, and x-ray pedestal 230 provide a safe, efficient transport of a patient or object between the two imaging systems. Patient transfers from one tabletop to another are unnecessary. Rather, the combination of patient transport table 210, patient cradle 220, and patient can move from one imaging system to another as a single unit, in a straight line of motion.

In an exemplary mode of operation, patient cradle 220 is retracted from the bore of the MR magnet of MR system 110 onto patient transport table 210. Patient transport table 210 can be undocked from MR system 110 and rolled into x-ray bay 125. As such, patient transport table 210 can be docked to x-ray pedestal 230 via an automatic, self-aligning latching system and patient cradle 220 is transferred onto the top of x-ray pedestal 230. Patient transport table 210 is moved out from under patient cradle 220 and the patient can be pivoted 90 degrees using x-ray pedestal 230 into position for use with an x-ray C-arm of x-ray system 120. The x-ray system C-arm can be located anywhere from +30° to +330° from the z axis of the MR system with respect to the x-ray pedestal.

Interlocks in x-ray pedestal 230 are provided to prevent un-latching patient cradle 220 from x-ray pedestal 230 until patient transport table 210 is in place to receive and support patient cradle 220. A reverse procedure can be followed to move the patient or object from x-ray bay 125 to MR bay 115.

As such, patient transport table 210, patient cradle 220, and x-ray pedestal 230 facilitate the location of an x-ray imaging system and a MR imaging system in a linear arrangement in adjacent rooms. The simple in-line transfer motion minimizes disruption to the patient, simplifies the transfer process for the operators, and minimizes the time required to transfer the patient from the x-ray system to the MR system. Further, all monitoring and support equipment travels with the patient eliminating relative motion between the patient and the equipment.

In an exemplary embodiment, patient transport table includes foot pedals for controlling docking, undocking, up movements, and down movements. For example, the dock pedal is pressed once the patient transport table is in a docking position. Once pressed, the dock pedal secures the transport table and releases the patient cradle. By way of another example, the up pedal can be pressed to raise the top of the patient transport to a desired height. The down pedal can be pressed and held to lower the top of the patient transport table to a desired height.

Figure 3:
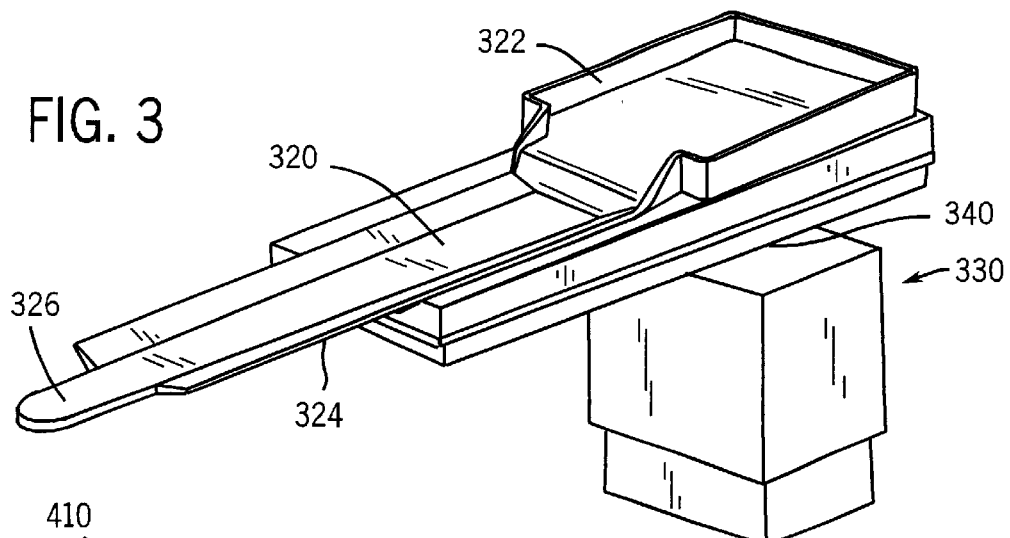
FIG. 3 is a diagrammatic representation of a patient cradle on an x-ray pedestal utilized in the X-MR suite of FIG. 1 in accordance with an exemplary embodiment.

FIG. 3 illustrates a patient cradle 320 on an x-ray pedestal 330 for use in X-MR suite 100 described with reference to FIG. 1. Patient cradle 320 can be configured to have a wide end section 322, a middle section 324, and a narrow end section 326. Patient cradle 320 can be fully cantilevered on x-ray pedestal 330 by a cantilever point 340. X-ray pedestal 330 is the only object supporting the patient during imaging. Advantageously, the x-ray beam only has to penetrate one support component.

Figure 4:
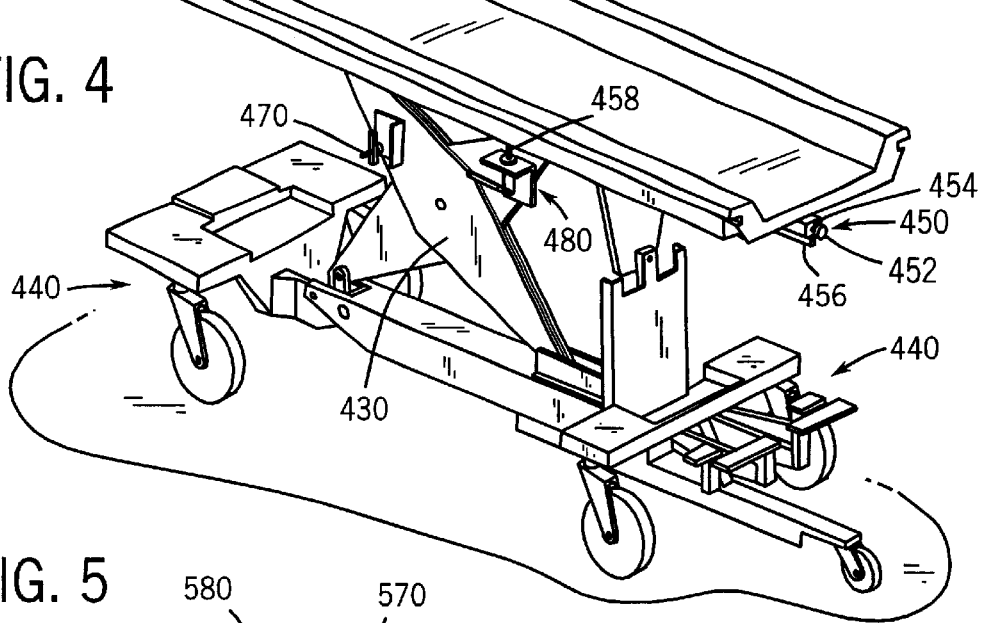
FIG. 4 is a perspective view diagrammatic representation of a patient transport table utilized in the X-MR suite of FIG. 1 in accordance with an exemplary embodiment.

FIG. 4 illustrates a patient transport table 410 for use in X-MR suite 100 described with reference to FIG. 1. Patient transport table 410 includes an elongated member 420 coupled to a support 430 and a transport assembly 440. Elongated member 420 can include docking interlocks 450 including two sets of position sensing interlocks to communicate docking information. Docking interlocks 450 can include spring mounted rods 452 and 454 that can be depressed by an analogous fixed position rod 456 when in a docked position. When spring mounted rods 452 and 454 are depressed, a cable is pulled releasing a spring and plunger assembly 458, thereby allowing a cradle positioned on elongated member 420 to move.

Patient transport table 410 also includes force/displacement levers 470 that are configured to enable cable actuation to pull another cable by a certain distance. Patient transport table 410 can also include a sensing assembly 480 that is configured to sense a cradle home position. Sensing assembly 480 can include spring and plunger assembly 458 and an automatic latch mechanism, allowing a simple, safe, and secure transfer process.

Figure 5:
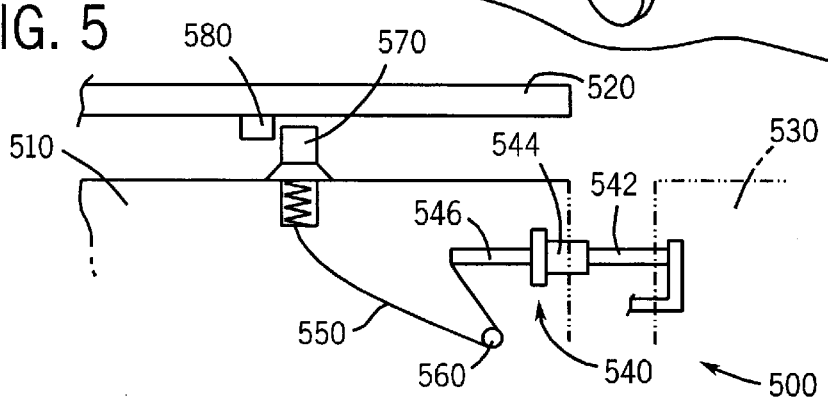
FIG. 5 is a cut-out diagrammatic representation of a docking mechanism utilized in the patient transport table of FIG. 4 in accordance with an exemplary embodiment.

FIG. 5 illustrates a docking assembly 500 included in a patient transport table 510 for docking with an x-ray pedestal 530 and transferring a cradle 520. Patient transport table 510 is similar to patient transport table 410 having docking interlocks 450 described with reference to FIG. 4. Docking assembly 500 can include a plunger assembly 540 in which a fixed position actuator 542 is coupled to a plunger 544 and an extended member 546. When plunger assembly 540 is depressed by the engaging of fixed position actuator 542 with pedestal 530, plunger assembly 540 moves a cable 550 about a pivot point 560, thereby retracting a locking tab 570. Once locking tab 570 is retracted, a cradle tab 580 coupled to cradle 520 is free to pass locking tab 570 and cradle 520 can be moved from patient transport table 510 to pedestal 530.

Figure 6:
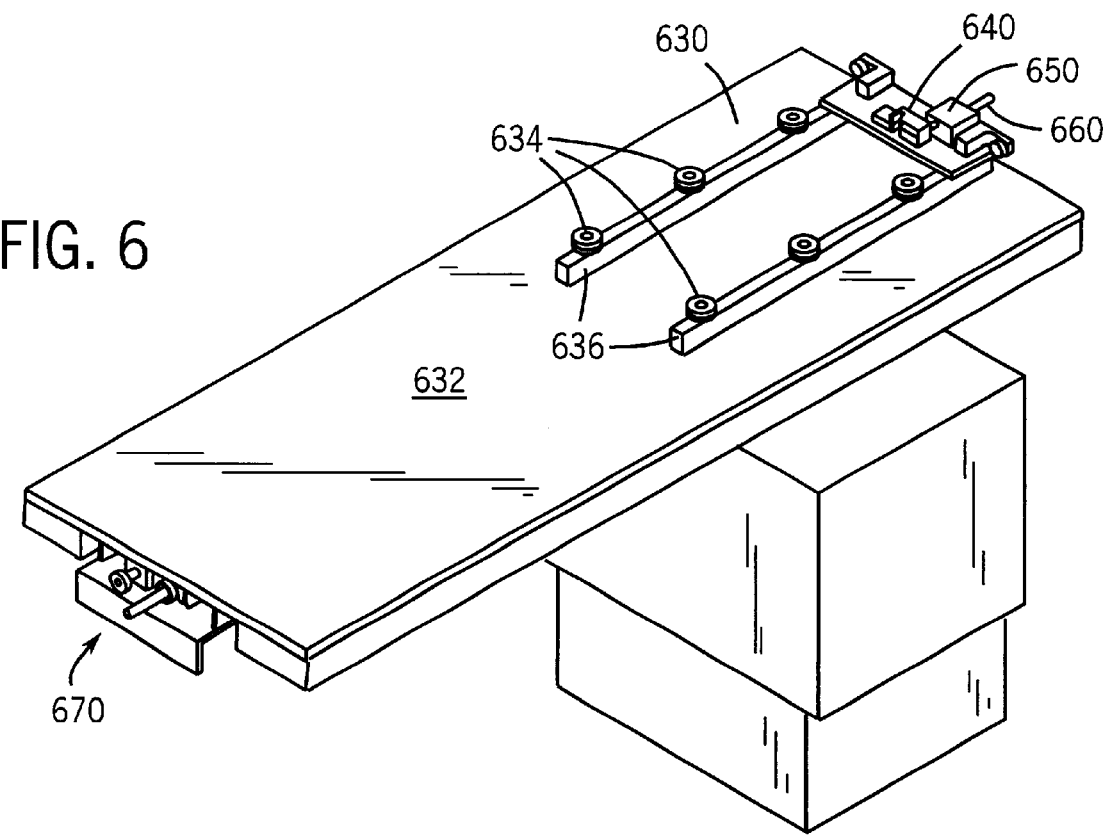
FIG. 6 is a perspective view diagrammatic representation of an x-ray pedestal utilized in the X-MR suite of FIG. 1 in accordance with an exemplary embodiment.

FIG. 6 illustrates an x-ray pedestal 630 for use in X-MR suite 100 described with reference to FIG. 1. X-ray pedestal 630 can include a planar section 632 whereupon a cradle holding a patient or other object of interest can be rested. Bearings 634 are located on guide rails 636 on planar section 632. Bearings 634 allow the cradle to smoothly slide on planar section 632 into a correct position on X-ray pedestal 630. Once the cradle is in position on X-ray pedestal 630, a cradle latch 640 is engaged to secure the cradle to X-ray pedestal 630. A cradle interlock assembly 650 is coupled to cradle latch 640 and is configured to prevent release of the cradle unless a patient transport table is docked to X-ray pedestal 630. A release lever 660 is also provided to manually release cradle latch 640.

X-ray pedestal 630 can also include docking components 670. Docking components 670 are configured as a mirror image of docking assembly 500 coupled to patient transport table 510 described with reference to FIG. 5. Docking components 670 can include a cable coupled to cradle interlock 650 that disengages cradle interlock assembly 650 when X-ray pedestal 630 is docked to a patient transport table and engages cradle interlock assembly 650 when x-ray pedestal 630 is not docked to the patient transport table.

Figure 7:
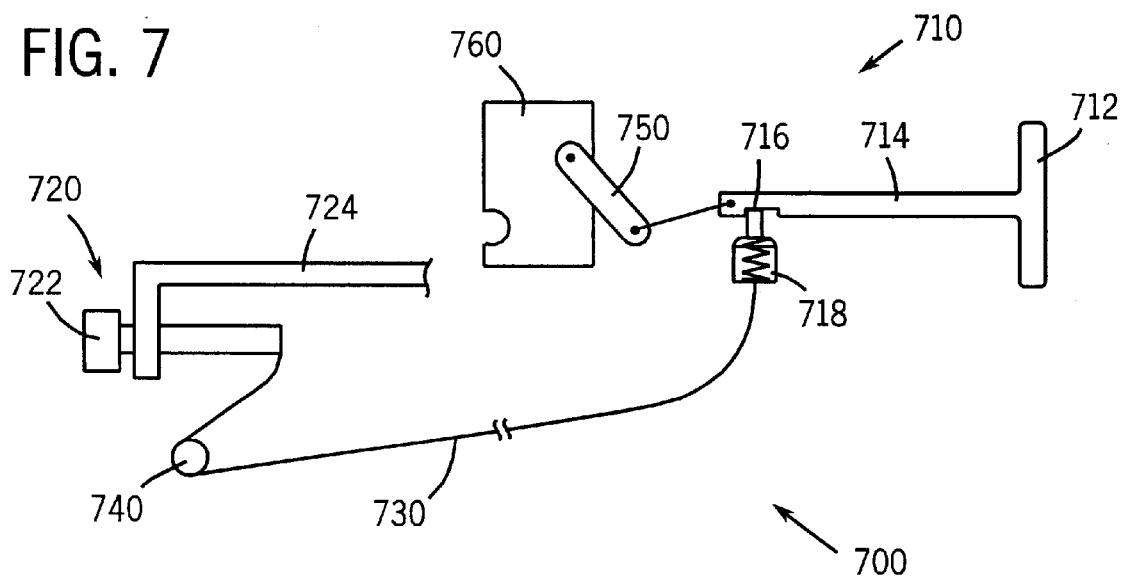
FIG. 7 is a cut-out diagrammatic representation of a cradle interlock system utilized in the X-ray pedestal of FIG. 6 in accordance with an exemplary embodiment.

FIG. 7 illustrates a cradle interlock system 700 included in x-ray pedestal 630 described with reference to FIG. 6. Cradle interlock system 700 can include a cradle interlock assembly 710 and a mating assembly 720. Cradle interlock assembly 710 can include a release handle 712 coupled to an elongated member 714. Elongated member 714 is coupled to a release 750 and a latch 760 that are configured to secure a cradle in place on an x-ray pedestal. Elongated member 714 can include a notch 716 that is configured to receive an interlock plunger 718.

When mating assembly 720 is in a docked position (i.e., a patient transport table is docked to an x-ray pedestal), a plunger 722 is pressed against a mating plate 724 such that a cable 730 is moved about a pivot point 740 and interlock plunger 718 is retracted from notch 716 of cradle interlock assembly 710. In use, therefore, mating assembly 720 makes it possible for cradle interlock assembly 710 to have handle 712 engage a release 750 and latch 760 such that a cradle on an x-ray pedestal can be released and moved onto a patient transport table docked to the x-ray pedestal.

Figure 8:
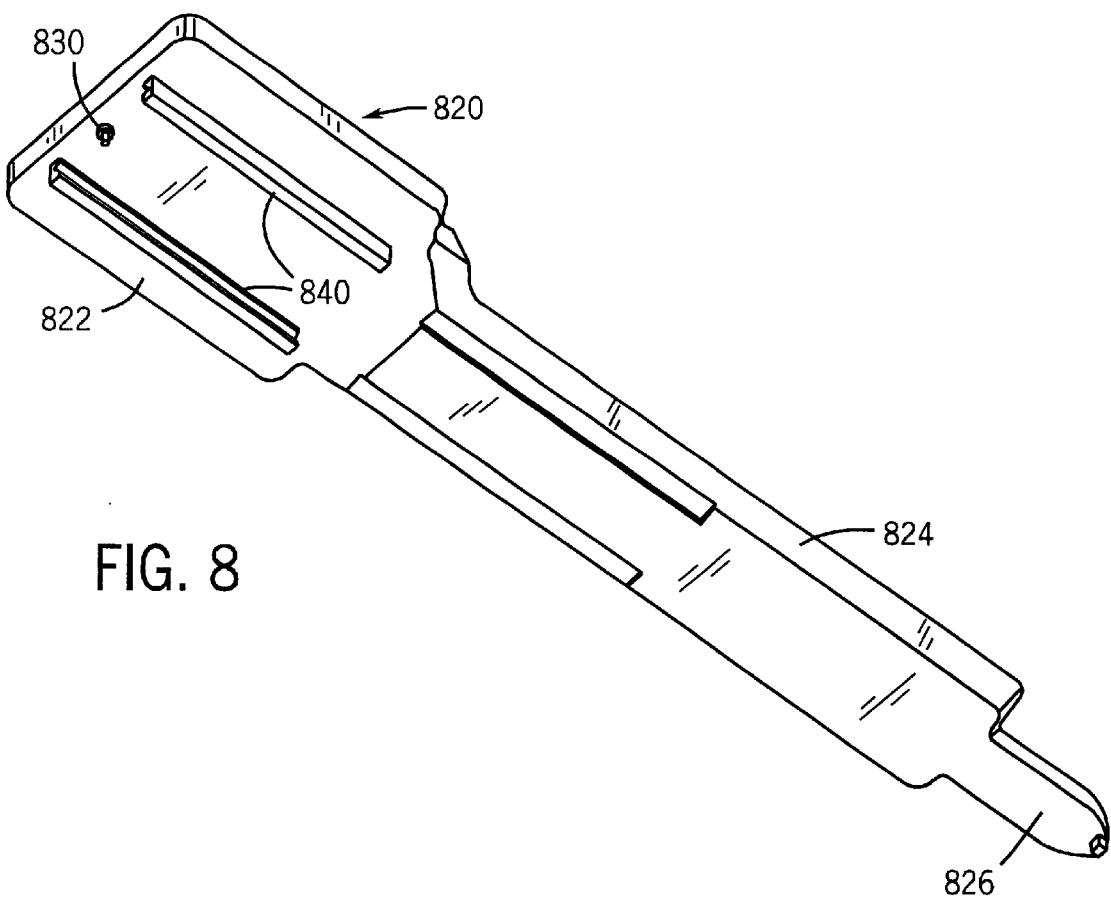
FIG. 8 is a perspective view diagrammatic representation of a patient cradle utilized in the X-MR suite of FIG. 1 in accordance with an exemplary embodiment.

FIG. 8 illustrates a patient cradle 820 that can be used on an x-ray pedestal such as x-ray pedestal 630 described with reference to FIG. 6. Patient cradle 820 can be an elongated member with a wide end 822, a middle 824, and a narrow end 826. At wide end 822, a cradle latch pin 830 is positioned on a side of patient cradle 820 opposite to a patient receiving side (i.e., a side facing the x-ray pedestal). Cradle latch pin 830 is configured to be received by cradle latching mechanisms, such as cradle latch 640 described with reference to FIG. 6.

Patient cradle 820 can also include rails 840 which are configured to be received by guide rails on an x-ray pedestal, such as, guide rails 636 described with reference to FIG. 6. In an exemplary embodiment, patient cradle 820 has an x-ray absorption characteristic of less than 1.0 mm aluminum equivalent.

Advantages of the transport system described with reference to the FIGS. 1–8 are numerous. For example, the system provides for mobile patient transport, allowing for patient setup outside of imaging bays. Further, multiple patient transports can be used to maximize throughput. The system allows a patient to be quickly transferred between imaging systems without lifting the patient. The dual end docking of the patient transport allows in line motion of the patient between systems, thus minimizing patient disruption.

Further advantages include the ability to use the xray system and MR system independently with the shielded door closed. Using the system, all monitoring and support equipment can be transferred with the patient, eliminating any relative motion between the patient and the equipment.

The patient cradle, patient transport table, and xray pedestal can be configured to have numerous different advantageous features. For example, the patient cradle or tabletop can be fully cantilevered on the x-ray pedestal so that x-ray absorption is minimized and image quality is optimized. The patient transport table and the x-ray pedestal can be configured to lock in position relative to each other to increase accuracy and safety while transferring the patient cradle. The patient cradle and the x-ray pedestal can feature a self-aligning engagement mechanism that simplifies the patient transfer process. The patient cradle and the x-ray pedestal can feature an automatic latching mechanism to ensure positive cradle capture.

While the exemplary embodiments illustrated in the FIGS. and described above are presently preferred, it should be understood that these embodiments are offered by way of example only. Other embodiments may include, for example, a variety of different interlocking mechanisms as well as a variety of patient cradle, transport table, and pedestal configurations. The invention is not limited to a particular embodiment, but extends to various modifications, combinations, and permutations that nevertheless fall within the scope and spirit of the appended claims.

What is claimed is:

1. A pedestal for supporting a patient or object of interest in an imaging system, the pedestal comprising:
   a support member being configured to support a patient or object of interest, the support member comprising a pivoting cantilever structure;
   an elongated planar member coupled to the support member and being configured to removably couple and slidably engage an elongated cradle member, the elongated planar member being fully cantilevered by the pivoting cantilever structure; and a docking assembly coupled to the elongated planar member configured to engage the receipt of and the removal of the elongated cradle member supportable by the elongated planar member.

2. The pedestal of claim 1, wherein the elongated cradle member is configured to rest on a movable patient transport table.

3. The pedestal of claim 2, wherein the docking assembly is configured to engage the receipt of the elongated cradle member from the movable patient transport table and engage the removal of the elongated cradle member to the movable patient transport table.

4. The pedestal of claim 2, wherein the docking assembly includes a cradle latch to secure the elongated cradle member once received from the movable patient transport table.

5. The pedestal of claim 1, wherein the docking assembly includes a mating assembly configured to allow for the release of a cradle latch securing the elongated cradle member to the elongated planar member.

6. The pedestal of claim 5, wherein the mating assembly is coupled to a cable that selectively immobilizes a handle coupled to the cradle latch.

7. The pedestal of claim 1, wherein the elongated cradle member has an x-ray absorption characteristic of less than 1.0 mm aluminum equivalent.

8. A patient support structure for use in an imaging system, the patient support structure comprising:

an elongated support surface including an end compatible with a coupling arrangement on a movable transport table configured to transport a patient cradle structure, the elongated support surface including a pivoting end coupled to a support member and configured to cantilever the elongated support surface about the support member; and a coupling device configured to removably couple the patient cradle structure to the elongated support surface, wherein the coupling device includes an actuator configured to disconnect the patient cradle structure from the elongated support surface.

9. The patient support structure of claim 8, further comprising guide rails positioned on the elongated support surface.

10. The patient support structure of claim 9, further comprising roller bearings coupled to the guide rails and configured to facilitate transfer of the patient cradle structure from the movable transport table to the elongated support surface.

11. The patient support structure of claim 8, wherein the patient cradle structure is suitable for use in a magnetic resonance imaging environment and an X-ray imaging system.

12. The patient support structure of claim 8, wherein the actuator is actuated by a human operator.

13. The patient support structure of claim 8, wherein the end compatible with the coupling device on the movable transport table includes a mating assembly detect the presence of the movable transport table and facilitate the transfer of the patient cradle structure.

* * * * *